United States Patent [19]

Zobel

[11] 4,274,704
[45] Jun. 23, 1981

[54] ENDOSCOPES INCORPORATING A BEAM SPLITTER

[75] Inventor: Jürgen Zobel, Bretten-Sprantal, Fed. Rep. of Germany

[73] Assignee: Richard Wolf GmbH, Knittlingen, Fed. Rep. of Germany

[21] Appl. No.: 63,073

[22] Filed: Aug. 2, 1979

[30] Foreign Application Priority Data

Aug. 25, 1978 [DE] Fed. Rep. of Germany ... 7825297[U]

[51] Int. Cl.³ .................... G02B 27/32; G02B 23/08
[52] U.S. Cl. ........................... 350/10; 350/52; 356/241
[58] Field of Search ............... 350/147, 50–53, 350/9–11; 128/4; 356/241

[56] References Cited

U.S. PATENT DOCUMENTS

| 2,372,430 | 3/1945 | Kals | 350/159 |
| 2,595,750 | 5/1952 | Back | 356/256 |
| 3,525,561 | 8/1970 | Takahashi | 350/10 |
| 3,582,178 | 6/1971 | Boughton et al. | 350/10 |
| 4,054,387 | 10/1977 | Whittome | 350/10 |

Primary Examiner—William H. Punter
Attorney, Agent, or Firm—Kinzer, Plyer, Dorn & McEachran

[57] ABSTRACT

This invention relates to endoscopes of the kind incorporating a beam splitter for direct observation and joint observation by means of a folded optical system substantially larger in diameter than the endoscope or for connection of a film or television camera to the folded optical system.

According to the invention, an opaque plate is mounted to face the folded optical system relative to the optical axis of a first part of said system in a tubular member the opaque plate having a small perforation arranged to pass light, the light spot of which is formed via a lens via the beam splitter via an achromatic lens with the image of the object in a common plane in a field lens and is guided together with the object image via the lens system of the folded optical system to an eye piece of the latter.

1 Claim, 1 Drawing Figure

U.S. Patent    Jun. 23, 1981    4,274,704
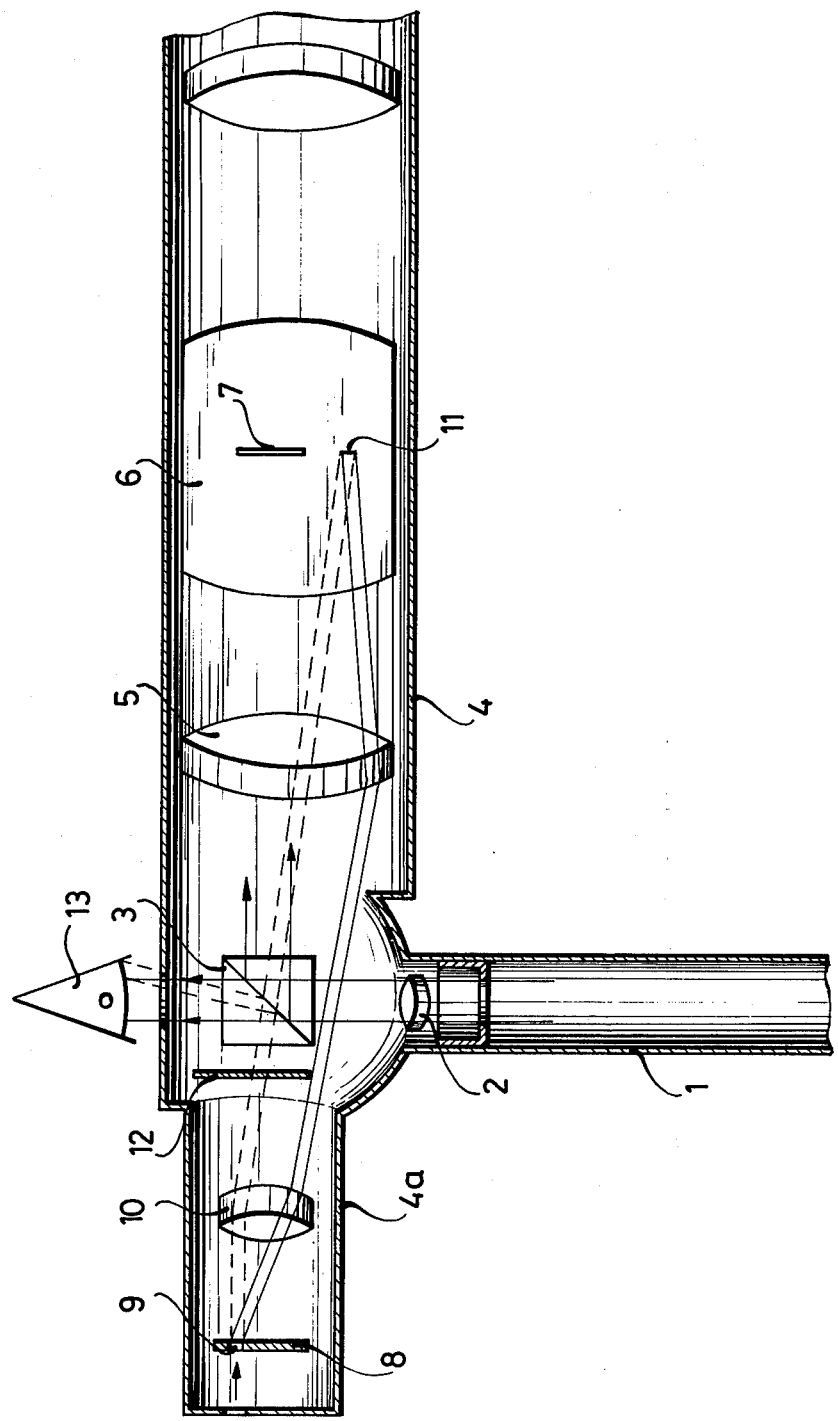

ENDOSCOPES INCORPORATING A BEAM SPLITTER

BACKGROUND OF THE INVENTION

The present invention relates to endoscopes of the kind incorporating a beam splitter for direct observation and for joint observation by means of a folded optical system of substantially larger diameter than the endoscope or for connection of a film or television camera to the folded optical system. Hereinafter such an endoscope will be referred to as "of the kind described".

Endoscopic images, which are supplied to the eye-piece of a co-observer by means of a beam splitter and a folded optical system, only occupy a correct horizontal and vertical position in the eye-piece in one particular position of the members of the folded optical system. As soon as any movement of the parts of the optical system is necessary for comfortable observation, deviations from this position occur and the image in the eye-piece is deflected by up to 180° in, for example, an anticlockwise direction so that the observer is no longer in a position to recognise what part of the image is at the top.

To eliminate this disadvantage marks have already been made in two parts of the folded optical system, that is in the eye-piece and lens parts which are made to overlap by swivelling the eye-piece member or by connecting links whereby correct positioning of the image for the co-observer occurs.

It is an object of the invention to provide means whereby the observer is able to recognise the actual position of the image and to adjust the image horizontally and vertically in the observer's eyepiece.

SUMMARY OF THE INVENTION

In an endoscope of the kind described the invention consists in that an opaque plate is mounted to face said folded optical system relative to the optical axis of a first part of said system in a tubular members said opaque plate having a small perforation arranged to pass light, the light spot of which is formed via a lens 10 via said beam splitter 3 via an achromatic lens 5 with the image of the object in a common plane in a field lens and is guided together with the object image via the lens system of said folded optical system to an eye piece of said folded optical system.

By means of this arrangement, the image together with the light spot appears in upright and correct lateral position in the eye-piece of the folded optical system with the light spot lying in juxtaposition above or below the image to denote the correct attitude of the image. If the folded optical system is moved the image may take up an altered position but the light spot also makes the same movement so that it always marks the position of the image correctly and thus provides orientation for the observer. The image and the light spot can, however, also be brought into an upright and laterally correct position again by suitable movement of the eye-piece member or also by intermediate members.

In general the brightness of the room is sufficient to create the light spot which forms through the perforation in the disc but the lightness can be increased if desired by a lamp to compensate for any possible vignetting in the folded optical system.

BRIEF DESCRIPTION OF THE DRAWINGS

In order that the invention may be more clearly understood, reference will now be made to the accompanying drawing which shows one embodiment thereof by way of example and in the form of:

of an endoscope incorporating a beam splitter and the objective member of a generally known folded optical system, the whole being schematically shown in axial section.

DETAILED DESCRIPTION OF PREFERRED EMBODIMENTS

Referring to the drawing, the image received by an endoscope 1 is delivered via an ocular 2 to eye 13 of the doctor via a beam splitter e.g. in the form of a prism 3 at the desired brightness whereas the same picture is reflected with the remaining proportion of brightness into the folded optical system 4 of which only the return lens (5) is shown. Then an upside-down endoscopic image 7 occurs in the first field lens 6 via achromatic return lens 5. The image is passed on via the parts or limbs of the folded optical system so that finally an upright, laterally correct image appears in a corrected position in the ocular of the folded optical system.

For recognition of displacements of the image and inclinations from an upright laterally correct image which occur when the parts or limbs of the folded optical system move, the housing is provided with a tubular member or support 4a with reference to the endoscope axis of the folding optical system. In this tubular member 4a is mounted an opaque plate 8 which is provided with a small perforation 9 radially spaced from the center of the tubular member. This perforation 9 can be circular, linear, square or cross-shaped. The perforation 9 lets light penetrate from the surrounding area or from a lamp (not shown) mounted before the tubular member 4a and the image thus resulting from the perforation 9 and the light spot from the perforation 9 is formed via a lens 10 through the beam splitter or at the beam splitter 3, via the achromatic lens 5, in the field lens 6 in the plane of the endoscopic image 7 at 11, i.e. in the case of the example, below the upside-down image 7.

When the image and light spot 11 formed by the perforation are retransmitted, the spot always turns with the image 7 and always remains in the same position in relation to the image until the image appears with the spot in the eye-piece of the folded optical system as an upright, laterally correct image. If then deviations in the position of the endoscopic image occur by movement of a limb of the folded optical system the spot 11 always remains in the same position relative to the image and gives the observer an orientation reference i.e. the observer will always recognise the location of the top of the image.

The light spot from perforation 9 by reflection under certain circumstances at the reflective face of the beam splitter causes the person 13 who is observing directly to be dazzled. To avoid this the beam splitter 3 can be shielded from the light spot e.g. by an opaque plate 12 and by blackening the face of the beam splitter facing the light spot so that the light spot is then guided past the beam splitter 3 into the folded optical system. The dazzling effect caused by the reflected light spot is, however, negligible for the direct observer if the beam splitter operates at a split ratio of 50:50 for example. Then the light spot from perforation 9 can be supplied directly to the beam splitter 3 without shielding as is indicated in dashed lines in the drawing.

I claim:

1. In an endoscope of the kind incorporating a beam splitter for simultaneous direct observation and joint observation, and also incorporating for joint observation an articulated optical system substantially larger in diameter than the endoscope shaft, or for alternative connection of a film or television camera to the last tube of the articulated optical system, which optical system includes within a first tube, fixed to the endoscope, both an achromatic lens and a field lens, the improvement in that an opaque plate (8) and related lens (10) are mounted in a tubular member relative to the axis of the endoscope (1) opposite to the first tube member of said articulated optical system, said opaque plate having a small opening radially spaced from the center of said tubular member arranged to pass light to said related lens, by which a spot or image of the opening is transmitted via, or adjacent the side of, said beam splitter to said achromatic lens (5) and in juxtaposition with the reflected image, reflected by the beam splitter, of the object of the endoscope in a common plane in said field lens (6), and said light spot then being guided in juxtaposition with the object image via the lens system of said articulated optical system to an eye piece of said articulated optical system so that at the eye piece the real attitude of the object is denoted by the light spot juxtaposed thereto.

* * * * *